(12) United States Patent
Yvin et al.

(10) Patent No.: US 7,671,040 B2
(45) Date of Patent: *Mar. 2, 2010

(54) CHEMOTHERAPEUTIC ANTINEOPLASTIC TREATMENT

(75) Inventors: Jean-Claude Yvin, Saint Malo (FR); Vaclav Vetvicka, Louisville, KY (US)

(73) Assignee: Laboratoires Goemar S.A., Saint-Malo (FR)

(*) Notice: Subject to any disclaimer, the term of this patent is extended or adjusted under 35 U.S.C. 154(b) by 406 days.

This patent is subject to a terminal disclaimer.

(21) Appl. No.: 10/668,661

(22) Filed: Sep. 23, 2003

(65) Prior Publication Data

US 2005/0065111 A1    Mar. 24, 2005

(51) Int. Cl.
*A61K 31/715*    (2006.01)
*A61K 31/716*    (2006.01)
*C08B 37/18*    (2006.01)

(52) U.S. Cl. .............. 514/54; 536/123.12; 536/123.1; 536/124

(58) Field of Classification Search .......... 514/54; 536/123.12, 123.1, 124
See application file for complete search history.

(56) References Cited

U.S. PATENT DOCUMENTS

| 6,117,850 A | 9/2000 | Patchen et al. |
| 6,660,722 B2 | 12/2003 | Yvin et al. |
| 2003/0119780 A1* | 6/2003 | Yvin et al. ............ 514/54 |

OTHER PUBLICATIONS

Luzio et al. (Progress in Cancer Research and Therapy (1978), 7 (Immune Modulation Control Neoplasia Adjuvant Ther.), 171-82). (Abstract Sent).*
Gura (Science, 1997, 278(5340):1041-1042).*
Jain (Sci. Am., 1994,271:58-65).*
Curti (Crit. Rev. in Oncology/Hematology, 1993, 14:29-39).*
Tsuzuki et al. (Bioscience, Biotechnology, and Biochemistry, (Jan. 1999) vol. 63, No. 1, pp. 104-110) (Abstract Sent).*
Chiba et al. (Pharmaceutical and Pharmacological Letters (1996), 6(1), pp. 12-15) (Abstract Sent).*
Fan et al. (Zhongguo Yaoke Daxue Xuebao (1988), 19 (1), pp. 30-34) (Abstract Sent).*

* cited by examiner

*Primary Examiner*—Shaojia Anna Jiang
*Assistant Examiner*—Michael C Henry
(74) *Attorney, Agent, or Firm*—B. Aaron Schulman; Stephen J. Weyer; Stites & Harbison PLLC

(57) ABSTRACT

Chemotherapeutic antineoplastic method comprising administration of an effective amount of an antineoplastic agent in conjunction with an effective amount of a β-1,3 glucan.

12 Claims, 2 Drawing Sheets

CHEMOTHERAPEUTIC ANTINEOPLASTIC TREATMENT

Figure 1:
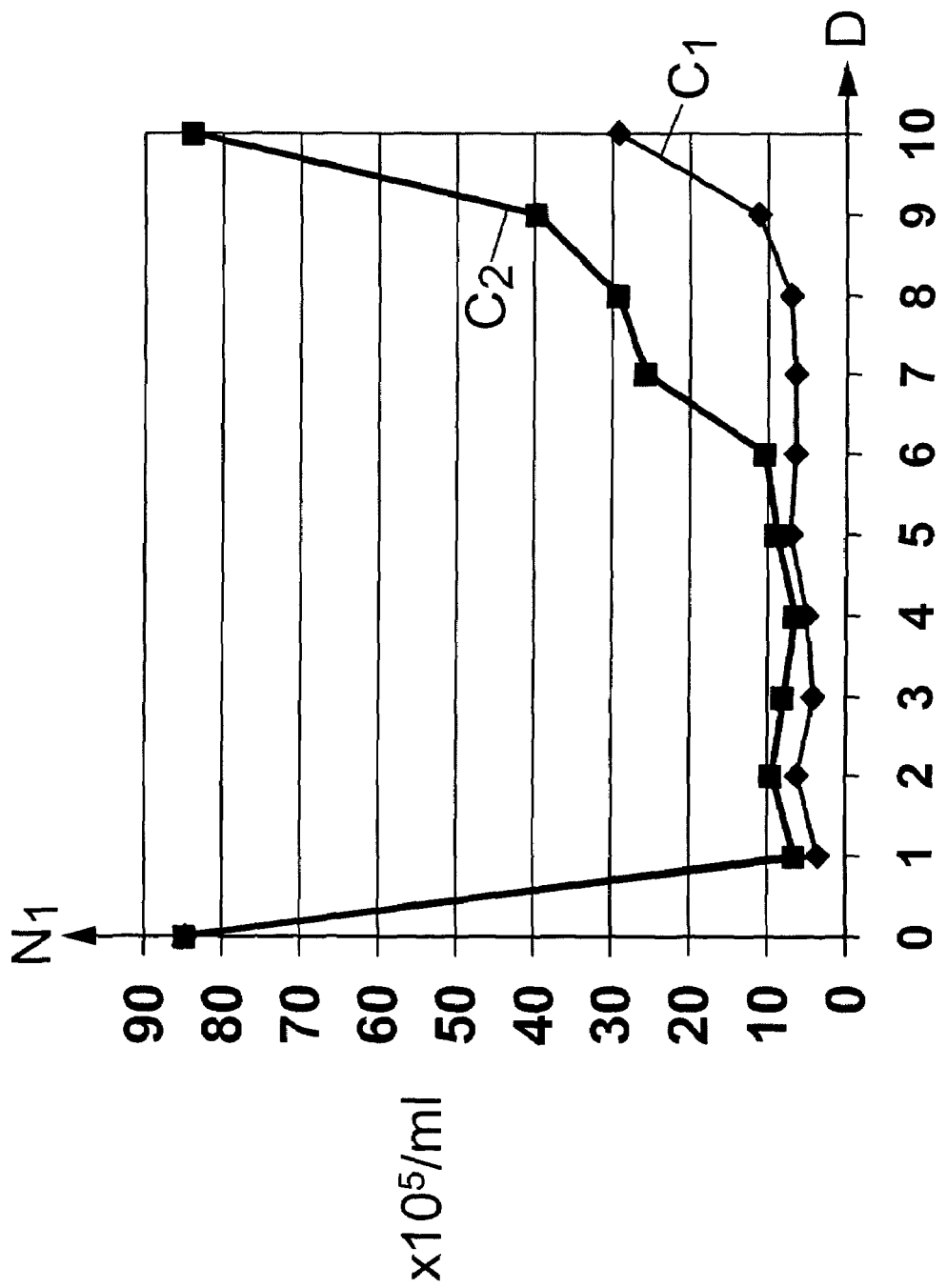

The use in chemotherapeutic antineoplastic treatments of antineoplastic agents, more commonly called "chemotherapy" drugs or agents, has increased these last years, due to the identification of new neoplasms and cancer cell types with metastases to different area, and due to the effectiveness of antineoplastic treatment protocols as a primary and adjunctive medical treatment for cancer.

These antineoplastic drugs are grouped conveniently into:

alkylating agents, anti-metabolites, naturally derived compounds, and miscellaneous drugs.

The most commonly used antineoplastic drugs are disclosed in Table I.

TABLE I

| ANTINEOPLASTIC AGENTS | | |
|---|---|---|
| Abbreviation | Generic | Brand in USA |
| HMM, HEXA | Altretamine | Hexalen (R) |
| A-ase, Asn-ase | Asparaginase | Elspar (R) |
| BCG | BCG | TheraCys (R), TICE BCG (R) |
| BLEO | Bleomycin sulfate | Blenoxane (R) |
| BU | Busulfan | Myleran (R) |
| CBDCA | Carboplatin | Paraplatin (R) |
| BCNU | Carmustine | BiCNU (R) |
| Chl | Chlorambucil | Leukeran (R) |
| CDDP, cis-DDP | Cisplatin-cis-platinum, cis-diammine-dichloroplatinum | Platinol (R), Platinol-AQ (R) |
| 2-CdA | Cladribine, 2-chlorodeoxyadenosine | Leustatin TM |
| CTX | Cyclophosphamide | Cytoxan (R), Neosar (R), generics |
| ARA-C | Cytarabine - cytosine arabinoside | Cytosar-U (R) |
| DTIC | Dacarbazine imidazole carboxamide | DTIC-DME, generics |
| DAC, ACT-D | Dactinomycin | Cosmegen (R) |
| DNR | Daunorubicin-daunomycin | Cerubidine (R) |
| DEX | Dexamethasone | Decadron (R), Tobradex (R) |
| DOX, ADR | Doxorubicin | Adriamycin (R), generics |
| VP-16 | Etoposide-epipodophyllotoxin | VePesid (R), generics |
| FUDR | Floxuridine | FUDR |
| 5-FU | Fluorouracil | Fluorouracil Injection |
| HALO | Fluoxymesterone | Halotestin (R) |
| FLU | Flutamide | Eulexin (R) |
| FLUD | Fludarabine | Fludara (R) |
| GOSE | Goserelin | Zoladex (R) |
| HU | Hydroxyurea | Hydrea (R) |
| IDA | Idarubicin HCL | Idamycin (R) |
| IFF, IFX | Ifosfamide - Isophosphamide | IFEX |
| IFN-a | Interferon alfa | Roferon (R)-A, Intron(R)-A |
| IFN-2a | Interferon alfa 2a | Roferon (R)-A |
| IFN-2b | Interferon alfa 2b | Intron (R)-A |
| IFN-3n | Interferon alfa n3 | Alferon (R)-N |
| CPT11 | Irinotecan | Camptosar (R) |
| Leu | Leucovorin calcium | Wellcovorin (R), generics |
| LEUP | Leuprolide | Lupron (R), Lupron-Depot (R) |
| LEV | Levamisole | Ergamisol (R) |
| CCNU | Lomustine | CeeNU (R) |
| MEGE | Megestrol | Megace (R) |

TABLE I-continued

| ANTINEOPLASTIC AGENTS | | |
|---|---|---|
| Abbreviation | Generic | Brand in USA |
| L-Pam, M, MEL | Melphalan - L-phenylalanine mustard, L-sarcolysin | Alkeran (R) |
| IV-M, IV-MEL | Melphalan Hydrochloride | IV Alkeran (R) |
| MESNA | MESNA | Mesnex (R) |
| HN(2) | Mechlorethamine, nitrogen mustard | Mustargen (R) |
| SOL | Metylprednisolone | Solumedrol (R), Medrol (R) |
| MTX | Methotrexate-Amethopterin | Methotrexate |
| MITC | Mitomycin-Mytomycin-C | Mutamycin (R) |
| DHAD, NOV | Mitoxantrone | Novantrone (R) |
| 6-MP | Mercaptopurine | Purinethol (R) Tablets |
| TAX | Paclitaxel | Taxol (R) |
| MITH | Plicamycin-Mithramycin | Mithracin (R) |
| Pred, P | Prednisone | Deltasone (R) |
| PCB | Procarbazine | Matulane (R) |
| STP | Streptozocin-Streptozotocin | Zanosar (R) |
| TAM | Tamoxifen | Nolvadex (R) |
| 6-TG | 6-thioguanine | Tabloid brand, Thioguanine (R) - |
| TSPA | Thiotepa-triethylene thiophosphoramide | Thiotepa |
| VLB | Vinblastine | Velban (R) |
| VCR | Vincristine | Oncovin (R) |
| NVB | Vinorelbine tartrate | Navelbine (R) Injection |

Various toxic effects ranging from eye, mucous membrane and skin irritations, to dizziness, nausea and headache, and more severe effects such as chromosomal aberrations, fetal loss, congenital malformation have occurred.

Among other side effects, bone marrow suppression causing depressions of the immune system and induction of leucopenia in most patients has been described.

Furthermore, chemotherapeutic antineoplastic treatments, in other words chemotherapy results in an acute reduction of the number of all cell types, particularly granulocytes in the organism consecutive to the administration of the antineoplastic drugs; the regeneration of the said cells is slow; due to the reduction of granulocytes, the treated patients become sensitive against infections and often must be kept isolated in sterile environments until the regeneration of the cells and in particular of the granulocytes is completed.

It follows that there is a permanent need for treatments capable of accelerating the regeneration of the cells, combating thus, in particular the induced leucopenia.

In that respect the Applicants have the merit of having found, after extensive research work that surprisingly and unexpectedly β-1,3 glucans whose molecular weight is from about 1000 to about 6000 and whose degree of polymerization is from about 5 to about 30, especially the well-known β-1,3 glucan called laminarin are capable when administered in conjunction with an antineoplastic agent to promote the regeration of the cells and in particular of the granulocytes reduced by the antineoplastic treatment.

Consequently, an object of the invention is a chemotherapeutic and especially an antineoplastic method comprising administration in conjunction with an antineoplastic agent, of a β-1,3 glucan, especially of laminarin, preferably of soluble laminarin.

Laminarin is extracted from brown algae and its molecular weight is from about 2500 to about 6000.

Laminarin is consisting of a main linear chain of 15 to 35 glucopyranose units joined by acetalic β-(1,3) linkages and to which a low proportion of branches, in essentially primary position of principally β-D-glucopyranose units are joined by β-(1,6) linkages, some of these β-D-glucopyranose units being joined to the main chain.

The average degree of polymerisation is close to 25.

The terminal unit of the main chain is consisting of glucose or of mannitol, thus providing two types of molecules respectively called G or M.

Complete hydrolysis provides glucose and manitol.

Two forms of laminarin have been identified; one of these forms is the here preferably used soluble form, while the other one is insoluble in water, the latter being probably caracterized by few or even no branches.

Both the soluble and the insoluble form may be obtained by extraction from e.g. *laminaria* species; two of these species are *laminaria digitata* and *laminaria hyperborea*.

Soluble laminarin occurs under the form of a white to beige powder which is odourless and tasteless; the soluble form is very hygroscopical and water-soluble (up to 60 g/l), while being substantially insoluble in ethanol, 2-propanol and acetone.

The identification of soluble laminarin may be carried out by way of liquid chromatography using, for example, a device comprising an amperometric detector.

Procedure may be as follows, using
- an anion-exchange column, fitted with a non-porous, polymeric resin whose particle size is about 5 μm, the length of the column being 250 mm and the internal diameter 4 mm,
- a pulsed amperometric detector equipped with a gold electrode,
- a mobile phase consisting of the mixture of a solution A with a solution B, the solution A initially representing 30% and the solution B 70%, the latter becoming isocratic of A after 4 minutes, which means that the mobile phase is only consisting of A.

Solution A is obtained by dissolving 41 g of sodium acetate in 950 ml of water, free of particles, and by introducing 8.2 ml of NaOH of 46-48%.

Solution B is a 150 mM solution of NaOH obtained by mixing 8.2 ml of NaOH of 47% with 990 ml of water, free of particles.

A quantity of 50 ml of the solution to be examined is injected and eluted at a rate of 1 ml/min during 15 minutes.

The thus obtained chromatogram comprises a Gauss pic of retention comprised between 5, 8 and 12 minutes, of maximum amplitude located at about 8 minutes.

The pH of a solution of 1 g of soluble laminarin in water, free of carbon dioxyde, completed to 10 ml, is from 6.5 to 7.5.

The combustion residue of 1 g of soluble laminarin is not higher than 5%.

The fucan content of soluble laminarin obtained by liquid chromatography dosing of the fucose content of the product obtained by total hydrolysis of the said soluble laminarin appears to be lower than 5%.

As mentioned hereabove, laminarin is extracted from brown macrophytic marine algae of the Pheophyceae type, in particular from *fucales* or *laminariales*.

Various extraction methods can be used.

Reference may be made for example to the method described by Black et al., Appl. Chem. 1951, 1, pages 505 to 517.

More generally, laminarin can be obtained from brown algae by any extraction process provided it enables the constituents other than laminarin (wall polysaccharides, salts. etc.) to be successively removed.

In particular, these processes use steps involving grinding, precipitation in an acid or basic medium, ultrafiltration and dialysis.

The thus obtained product is consisting of a mixture of the soluble and the insoluble forms of laminarin, the respective proportions of which vary according to the selected algae.

For example, *laminaria digitata* or *laminaria saccharina* provide a mixture comprising about 90% by weight of the soluble form, while *laminaria hyperborea* provides a mixture comprising about 80% by weight of the insoluble form.

The latter is separated by precipitation.

The following non-limiting example illustrates the extraction process of soluble laminarin.

300 g of fresh algae of the *Laminaria saccharina* type, harvested in August, are subjected to cryobursting (−40° C.) by the process described in French patent no. 74 35162.

The product thus obtained has a mean particle diameter of between 50 and 100 μm and a solids content of 10-12%. A quantity of 0.9 l of 0.3% sulfuric acid is added gradually to 300 g of this product. Extraction is performed in a water bath at a temperature of about 80° C., for 1 hour, with stirring.

This operation is repeated twice.

After neutralization, the extract obtained is treated with polyvinylpyrrolidone in a dose of about 1% by weight. This is done by introducing 9 g of polyvinylpyrrolidone (PVP) into a volume of 90 ml of extract. The PVP is left to thicken for about 2 hours. The resulting solution is added to about 0.9 liter of extract, the mixture being stirred for 30 min and then filtered under vacuum on a Whatman GF/A filter.

The thus obtained liquid is subjected to tangential ultrafiltration on a carbon-ceramic tubular membrane of the "Carbosep" type with a porosity of 50.000 Daltons. A pressure of 1 bar is maintained on the filtration column during the operation.

This gives a filtrate having a volume of about 0.8 liter and a pH of 5.5. The filtrate is maintained about one night at about 4° C.; the precipitated insoluble form of laminarin is removed by filtration and the thus treated filtrate is then dialyzed on a cellulose ester membrane of the SPECIRA Pore type with a porosity of 500 or 1000 Daltons. The dialyzate is then lyophilized to give 7 g of dry powder, corresponding to pure soluble laminarin.

In the course of the studies and searches which lead to the instant invention and which were carried out using especially soluble laminarin, the Applicants more particularly performed experimentations which enabled the determination of the ability of β-1,3 glucan and especially of laminarin to promote the regeneration of all the cells and in particular of the granulocytes reduced in patients treated with antineoplastic agents or drugs.

In that respect, Applicants carried out in vivo assays on Balb/c mice by the hereafter disclosed methods.

These tests were conducted to evaluate the promoting effects of laminarin on the regeneration of all the cells reduced in mice treated with an antineoplastic drug.

In that connection, the mice were treated on the one hand with an antineoplastic drug alone and, on the other hand with the same antineoplastic drug in conjunction with laminarin.

The antineoplastic drug used in the hereafter disclosed experimentation is cyclophosphamide.

The laminarin is soluble laminarin.

The experimentation consisted in the determination in bone marrow and in peripheral blood of the regeneration of all the cells reduced by the antineoplastic drug.

a) Determination in Bone Marrow.

A first group and a second group comprising each 50 mice of the Balb/c type were tested.

On day 0 the mice of the first group were injected with cyclophosphamide alone and those of the second group with cyclophosphamide and immediately after with laminarin.

The injection was an intraperitoneally injection.

The cyclophosphamide purchased from SIGMA, St Louis, USA was dissolved for injection in phosphate buffered saline from SIGMA.

The amount of injected cyclophosphamide corresponds to about 25 mg per mouse having a weight of about 25 g.

The amount of injected laminarine, also diluted in phosphate buffered saline, corresponds to about 250 µg per mouse.

On day 0 and then each day after day 0, during 10 days, the total number of cells per ml in bone marrow was determined on several mice of each of both first and second groups.

The number of cells in bone marrow was evaluated as hereafter disclosed. The mice were killed by cervical dislocation, placed on their back on cutting board and soaked with ethanol. A long traverse cut through the skin in the middle of the abdominal area was followed by reflecting the skin from the hindquarters and the hind legs. The legs were separated from the body at the hip joint and the feet were removed. The legs were placed in a Petri dish obtaining RPMI 1640 medium (Sigma). All muscle tissue from the femurs and tibia was removed and the bones were separated (only femurs were used). The epiphyses were cut off on both ends, the bone end was punctured with a 23 G needle and flushed out with 3 ml of warm (22° C.) RPMI 1640 medium. The large debris and cell clumps were removed by layering the cell suspension over 3 ml of heat-inactivated fetal calf serum (FCS; Hyclone, Logan, Utah, USA) for 10 minutes on ice. The cells collected from the top of FCS were washed once by centrifugation at 300×g for 10 minutes at 4° C. and kept in RPMI 1640 medium containing 5% FCS. Five microliters of the cell suspension was mixed with 95 ul of Turk's solution (a mixture of 3 ml concentrated acetic acid, 3 ml of 1% crystal violet in water, Fernandez-Botran and Vetvicka "Methods in Cellular Immunology", CRC Press, Boca Raton, 1995), and incubated for 5 minutes at room temperature. One drop of this solution has been dropped into a hemocytometer and the cells were counted under an optical microscope.

The result of the counting is expressed in number of cells per femur×$10^6$.

b) Determination in Peripheral Blood

The peripheral blood of the mice of the first and the second groups of mice under experimentation according to a) was used to determine the total number of all cells on day 0 and then on each of the following days until day 10 on several mice selected from each of the first and the second groups.

The number of cells in peripheral blood has been evaluated as hereafter disclosed. One drop of blood from the orbital plexus was mixed with 95 ul of Turk's solution (a mixture of 3 ml concentrated acetic acid, 3 ml of 1% crystal violet in water and 294 ml of water, Fernandez-Botran and Vetvicka "Methods in Cellular Immunology", CRC Press, Boca Raton, 1995), and incubated for 5 minutes at room temperature. One drop of this solution has been dropped into a hemocytometer and the cells were counted under an optical microscope.

The result of the counting is expressed in number of cells per ml of peripheral blood×$10^5$.

c) The Results of the Countings Carried Out According to A) and B) are Recorded in Tables IIa and IIb.

In Table IIa is indicated the number of cells in peripheral blood and in bone marrow of the mice intended to be subjected to the experimentation but before injection of either cyclophosphamide alone or in conjunction with laminarin.

Consequently three mice were sacrified and the number of cells was determined in peripheral blood and in bone marrow, proceeding as hereabove indicated.

The average number of cells is also indicated.

TABLE IIa

| | Before injection (control) on Day 0 Number of cells | |
|---|---|---|
| | In peripheral blood per ml × $10^5$ | In bone marrow per femur × $10^6$ |
| Mouse 1 | 130 | 13.5 |
| Mouse 2 | 51.3 | 12.8 |
| Mouse 3 | 72.8 | 12.3 |
| Average | 84.7 | 12.9 |

Then, the first and the second groups of mice are constituted.

Cyclophosphamide alone is injected to the mice of the first group and cyclophosphamide followed by laminarin is injected to the mice of the second group.

The day at which these injections were performed is called day 0.

The results of the experimentations carried out from day 1 to day 10 are collected in Table IIb.

On day 1, four mice of the first group and three mice of the second group were sacrified and the number of cells was determined in peripheral blood and in bone marrow of each of these four and three mice, the average value being calculated.

On each of days 2, 3, 5, 6, 7, 8, 9 and 10, three mice of each group were sacrified, the number of cells in peripheral blood and in bone marrow being determined for each mouse and the average value being calculated in each case.

On day 4 however, four mice of each group were sacrified, the number of cells being determined for each mouse and the average value being calculated.

TABLE IIb

After injection of cyclophosphamide alone to the mice of the first group and of cyclophosphamide followed by laminarine to the mice of the second group
NUMBER OF CELLS

| | | First group | | Second Group | |
|---|---|---|---|---|---|
| Day | Mice | Peripheral blood per ml × $10^5$ | Bone marrow per femur × $10^6$ | Peripheral blood per ml × $10^5$ | Bone marrow per femur × $10^6$ |
| 1 | Mouse 1 | 5.1 | 1.4 | 6.4 | 2.8 |
| | Mouse 2 | 3.0 | 1 | 7.2 | 2.1 |
| | Mouse 3 | 3.8 | 1.2 | 5.8 | 2.3 |
| | Mouse 4 | 2.4 | 1.4 | | |

TABLE IIb-continued

After injection of cyclophosphamide alone to the mice of the first group and of cyclophosphamide followed by laminarine to the mice of the second group
NUMBER OF CELLS

| | | First group | | Second Group | |
|---|---|---|---|---|---|
| Day | Mice | Peripheral blood per ml × $10^5$ | Bone marrow per femur × $10^6$ | Peripheral blood per ml × $10^5$ | Bone marrow per femur × $10^6$ |
| | Average | 3.6 | 1.25 | 6.5 | 2.4 |
| 2 | Mouse 1 | 6.6 | 0.8 | 10.2 | 2.8 |
| | Mouse 2 | 6.0 | 2.0 | 9.0 | 5.8 |
| | Mouse 3 | 6.3 | 2.4 | 8.8 | 5.9 |
| | Average | 3.6 | 1.25 | 6.5 | 2.4 |
| 3 | Mouse 1 | 3.8 | .4 | 9.8 | 5.5 |
| | Mouse 2 | 3.8 | 5.0 | 5.8 | 3.0 |
| | Mouse 3 | 5.1 | 3.3 | 7.8 | 4.0 |
| | Average | 4.2 | 3.6 | 7.8 | 4.2 |
| 4 | Mouse 1 | 5.8 | 2.1 | 9.2 | 2.5 |
| | Mouse 2 | 4.7 | 3.8 | 6.9 | 15.3 |
| | Mouse 3 | 5.2 | 3.5 | 1.6 | 6.8 |
| | Mouse 4 | 4.8 | 1.2 | 7.8 | 6.3 |
| | Average | 5.1 | 2.7 | 6.4 | 7.7 |
| 5 | Mouse 1 | 4.0 | 2.1 | 5.4 | 10.2 |
| | Mouse 2 | 9.6 | 6.0 | 10.8 | 2.5 |
| | Mouse 3 | 8.1 | 6.1 | 10.5 | 8.8 |
| | Average | 7.2 | 4.7 | 8.9 | 7.2 |
| 6 | Mouse 1 | 7.8 | 6.5 | 8.8 | 3.2 |
| | Mouse 2 | 5.0 | 5.7 | 10.6 | 16.4 |
| | Mouse 3 | 6.7 | 7.0 | 11.9 | 10.5 |
| | Average | 6.5 | 6.4 | 10.4 | 10.0 |
| 7 | Mouse 1 | 3.8 | 9.0 | 19.2 | 13.9 |
| | Mouse 2 | 7.3 | 8.1 | 25.4 | 14.1 |
| | Mouse 3 | 8.1 | 7.3 | 31.9 | 13.2 |
| | Average | 6.4 | 8.1 | 25.5 | 13.7 |
| 8 | Mouse 1 | 4.1 | 6.0 | 18.4 | 12.1 |
| | Mouse 2 | 8.2 | 6.2 | 18.9 | 12.8 |
| | Mouse 3 | 9.3 | 6.8 | 39.8 | 14.5 |
| | Average | 7.2 | 6.3 | 29.0 | 13.1 |
| 9 | Mouse 1 | 8.9 | 8.0 | 20.6 | 15.9 |
| | Mouse 2 | 11.9 | 8.5 | 41.3 | 10.5 |
| | Mouse 3 | 12.9 | 8.2 | 57.5 | 12.9 |
| | Average | 11.2 | 8.2 | 39.8 | 13.1 |
| 10 | Mouse 1 | 23.8 | 7.2 | 41.5 | 12.9 |
| | Mouse 2 | 27.8 | 10.8 | 89.9 | 13.1 |
| | Mouse 3 | 35.9 | 10.3 | 120.4 | 14.3 |
| | Average | 29.2 | 9.4 | 83.9 | 13.4 |

Figure 2:
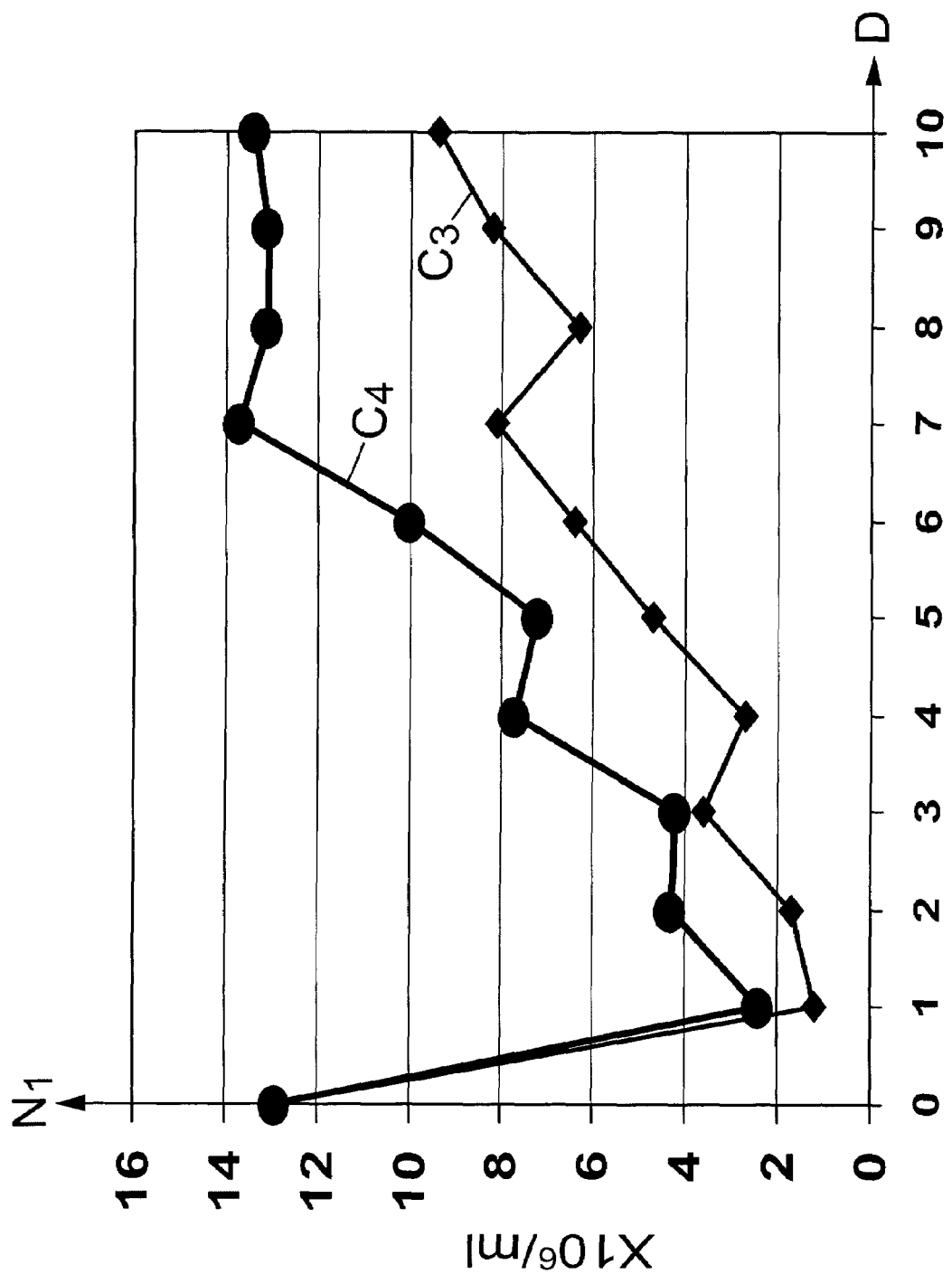

The average or mean numbers of cells calculated each day D from day 1 to day 10 in peripheral blood (mean number $N_1$) and in bone marrow (mean number $N_2$) were indicated as a function of the day on the graph shown in FIG. 1 as far as the cells counted in peripheral blood are concerned providing thus a curve $C_1$ corresponding to the injection of cyclophosphamide alone and a curve $C_2$ corresponding to the injection of cyclophosphamide followed by laminarine;

on the graph shown in FIG. 2 as far as the cells counted in bone morrow are concerned providing thus a curve $C_3$ corresponding to the injection of cyclophosphamide alone and a curve $C_4$ corresponding to the injection of cyclophosphamide followed by laminarine.

The comparison of the average or mean numbers of cells collected in Tables Ia and Ib and still more clearly the comparison of curves $C_1$ and $C_2$ on the one hand and of curves $C_3$ and $C_4$ on the other hand show that when administering laminarin in conjunction with cyclophosphamide the regeneration of the cells is significantly improved.

Thus the method of chemotherapeutic antineoplastic treatment according to the invention leads to a dramatic decrease of the well-known side effect which consists in the reduction of cells in the organism of a patient when administering antineoplastic agents.

Consequently an object of the invention is consisting in an chemotherapeutical antineoplastic treatment or method comprising administration of an effective amount of an antineoplastic agent in conjunction with an effective amount of β-1,3 glucan having a molecular weight from about 1000 to about 6000 and a degree of polymerization from about 5 to about 30, especially laminarin.

The expression "effective amount" designates throughout the specification, as far as the antineoplastic agent is concerned, the commonly used and well-known amounts of these medicines and as far as the β-1,3 glucan is concerned the amount per kg of the patient which permits to obtain the best regeneration rate of the cells.

The antineoplastic agents may be selected from the table I.

The β-1,3 glucan and especially laminarin can be administered orally, intravenously or intraperitoneally.

As above indicated, the antineoplastic agents are commonly administered orally or intravenously and the amounts administered are those used in the art.

Due to the efficiency of the β-1,3 glucan an increase of the amounts of administered antineoplastic agents can be contemplated.

The β-1,3 glucan and especially laminarin is administered before, simultaneously to or after the antineoplastic agent.

The contemplated antineoplastic treatment involves as far as the β-1,3 glucan and especially laminarin is concerned, the posologies and the pharmaceutical forms hereafter disclosed.

Dosages vary depending essentially on the mode of administration, i.e. whether the intravenously or the oral route is selected.

In that respect when administrated intravenously the dosis of soluble laminarin is from about 0.1 to 10 mg per day.

By oral administration, the dosis vary from about 1 to about 100 mg/kg and is preferably of about 10 mg/kg, advantageously twice a week over extended periods of time and possibly for the whole life of the patient.

A further object according to the invention is consisting in a therapeutic antineoplastic method comprising the administration of ENDOXAN ASTRA® (cyclophosphamide) intravenously at a standard posology of 500 mg/adult during 1 hour followed by intravenous injection of 10 mg of laminarin. This injection is renewed each day during 7 days.

A further object according to the invention is consisting in a therapeutic antineoplastic method comprising the administration of ENDOXAN ASTRA® (cyclophosphamide) intravenously at a standard posology of 500 mg/adult during 1 hour followed by an oral administration of one tablet of 1 g of laminarin. This treatment could be renewed once after 7 days.

Laminarin, especially in its soluble form is considered as safe.

Its LD 50 is high and was determined as to be greater than 2000 mg/kg given orally in rats; furthermore there are no special handling requirements.

It is possible to contemplate medicinal formulations which comprise both the antineoplastic agent and the β-1,3 glucan, the antineoplastic agent being present under one of its usual formulations and the β-1,3 glucan, especially laminarin, in the form of pulverulent soluble laminarin mixed with a pharmaceutically acceptable carrier.

The "pharmaceutical acceptable carrier" is selected from the group comprising pharmaceutically acceptable solvents, suspending agents or vehicles, and in function of the route selected for administration, and keeping in mind standard pharmaceutical practice; "acceptable" means that the carrier is compatible with the other ingredients of the formulation and with the antineoplastic agent and not injurious to the patient.

More generally, a "pharmaceutically acceptable component" should not present or induce undue adverse side effects such as toxicity, irritation, and allergic response and should be commensurate with a reasonable benefit/risk ratio.

Oral formulations of β-1,3 glucan and especially of laminarin suitable for use in connection with the present invention include capsules, gels, cachets, effervescent or non-effervescent powders, tablets, and granules; they may consist of a solution, of a suspension in an aqueous or non-aqueous liquid, of an oil-in-water liquid emulsion or of a water-in-oil emulsion.

The pharmaceutical forms through which laminarin is administered may also be presented as a bolus, an electuary, or a paste.

Generally, the said formulations may be prepared by uniformly mixing the active ingredient, i.e. especially soluble laminarin with liquid carriers or finely divided solid carriers or both, and then if necessary by shaping the product.

Suitable solid carriers comprise lactose, sucrose, gelatin, agar and bulk powders.

Suitable liquid carriers comprise water, pharmaceutically acceptable fats and oils, alcohol or other organic solvents, including esters, emulsions, syrups or elixirs, suspensions, solutions and/or suspensions, and solutions and or suspensions reconstituted from non-effervescent granules and effervescent preparations reconstituted from effervescent granules.

They also may comprise preservatives, emulsifying agents, suspending agents, diluents, sweeteners, thickeners, and melting agents; preferred liquid carriers are edible oils, for example, corn or canola oils, as well as polyethylene glycols or PEG.

The therapeutical forms, intented for oral administration, comprise non-toxic, pharmaceutically acceptable, inert carriers selected from the group comprising lactose, starch, sucrose, glucose, methyl cellulose, magnesium stearate, dicalcium phosphate, calcium sulfate, mannitol, sorbitol, cyclodextrin, and cyclodextrin derivatives.

Capsules or tablets containing laminarin according to the invention should preferably be easy to swallow or to chew, and contain carriers, binders, lubricants, diluents, disintegrating agents, coloring agents, flavoring agents, flow-inducing agents, or melting agents; they may be produced by compression or molding, optionally with one or more classical additional ingredients.

The tablets are optionally coated and may be formulated so as to provide slow- or controlled-release of the active ingredient. Tablets may also optionally be provided with an enteric coating to provide release in parts of the gut other than the stomach.

EXAMPLE A

Laminarin Containing Tablet

A large number of tablets are prepared by conventionnal procedures so that the dosage unit was 100 mg of active ingredient per tablet:

| | |
|---|---|
| soluble laminarin in lyophylised form | 100 mg |
| colloidal silicon dioxide | 0.2 mg |
| Magnesium stearate | 5 mg |
| Microcristalline cellulose | 270 mg |
| Starch | 10 mg |
| Mannitol | 98.8 mg |

Appropriate coating can be applied to increase palatability and or delay absorption.

EXAMPLE B

Laminarin Containing Granules

An amount of 1 liter of an aqueous solution containing 75 g of soluble laminarin is mixed with 10 g of dextrin, the thus obtained mixture being absorbed into a food base i.e starch, sorbitol, carboxy-methyl-cellulose, lactose, mannitol, guar gum, vanilline.

The resulting powder is extruded to form an extrusion granulate using a net of 1 mm. The granules are sieved on a 12 mesh sieve and the resulting granules are dried at 60° C. overnight in a drier to provide granules containing about 25% by weight of laminarin and about 3% of moisture.

These granules are used as an additive to drinking water or the like. For example, for these granules, a posology of 6 to 9 tea spoons per day for and adult and 2 or 3 tea spoons per day for a children is recommanded.

EXAMPLE C

Lozenges for oral administration containing insoluble laminarin comprise

| insoluble laminarin powder | 5 parties by weight |
| mannitol as flavored carrier | 20 parties by weight |
| starch | 25 parties by weight |
| sorbitol | 30 parties by weight |
| sucrose | 20 parties by weight |

The invention claimed is:

1. Method to promote the regeneration of the cells in the bone marrow and the peripheral blood of a patient subjected to a chemotherapeutic antineoplastic treatment comprising administration to said patient of an effective amount of an antineoplastic agent that causes an acute reduction of said cells, said method comprising administration of laminarin to the patient in an amount effective to cause promotion of the regeneration of the cells, the laminarin being administered in conjunction with the administration of the antineoplastic agent, wherein said laminarin:

has a molecular weight from about 2,500 to about 6,000, and consists essentially of a main linear chain of 15 to 35 glucopyranose units joined by β-(1,3) linkages optionally branched with glucopyranose units linked to the main chain by β-(1,6) linkages, the terminal unit of the main chain being selected from the group consisting of glucose and mannitol.

2. Method according to claim 1 wherein the antineoplastic agent is cyclophosphamide.

3. Method according to claim 1 wherein the laminarin is administered orally, intravenously or intraperitoneally.

4. Method according to claim 2 wherein laminarin is administered orally, intravenously or intraperitoneally.

5. Method according to claim 1 wherein laminarin is administered before, simultaneously with or after the antineoplastic agent.

6. Method according to claim 2 wherein laminarin is administered before, simultaneously with or after cyclophosphamide.

7. Method according to claim 1 wherein laminarin is soluble laminarin.

8. Method according to claim 2 wherein laminarin is soluble laminarin.

9. Method according to claim 3 wherein laminarin is soluble laminarin.

10. Method according to claim 4 wherein laminarin is soluble laminarin.

11. Method according to claim 5 wherein laminarin is soluble laminarin.

12. Method according to claim 6 wherein laminarin is soluble laminarin.

* * * * *